US010034723B2

(12) United States Patent
Mozaffari et al.

(10) Patent No.: US 10,034,723 B2
(45) Date of Patent: Jul. 31, 2018

(54) TOOTH BRACKET EXTRACTION DEVICE AND METHODS FOR EXTRACTING A BRACKET SECTION FROM TEETH

(71) Applicants: Abdolhossein Mozaffari, Tehran (IR); Mohsen Shirazi, Tehran (IR)

(72) Inventors: Abdolhossein Mozaffari, Tehran (IR); Mohsen Shirazi, Tehran (IR)

(*) Notice: Subject to any disclaimer, the term of this patent is extended or adjusted under 35 U.S.C. 154(b) by 71 days.

(21) Appl. No.: 15/338,367

(22) Filed: Oct. 29, 2016

(65) Prior Publication Data
US 2018/0116765 A1    May 3, 2018

(51) Int. Cl.
*A61C 7/02* (2006.01)
*A61C 7/14* (2006.01)
*A61C 1/18* (2006.01)
*F16H 1/14* (2006.01)

(52) U.S. Cl.
CPC .......... *A61C 7/023* (2013.01); *A61C 1/186* (2013.01); *A61C 7/146* (2013.01); *F16H 1/14* (2013.01)

(58) Field of Classification Search
CPC .............. A61C 7/023; A61C 1/186
See application file for complete search history.

(56) References Cited

U.S. PATENT DOCUMENTS

| | | | |
|---|---|---|---|
| 3,309,965 A | 3/1967 | Weickgenannt | |
| 4,776,791 A * | 10/1988 | Hannula | A61C 7/04 433/4 |
| 4,904,183 A * | 2/1990 | Hannan | A61C 7/02 433/3 |
| 4,950,157 A * | 8/1990 | Cleary | A61C 7/02 433/4 |
| 5,035,612 A * | 7/1991 | Martin | A61C 7/02 433/3 |
| 5,295,831 A * | 3/1994 | Patterson | A61C 8/0089 433/141 |
| 5,366,372 A * | 11/1994 | Hansen | A61C 7/02 433/4 |
| 5,543,695 A * | 8/1996 | Culp | A61C 1/0015 318/432 |
| 6,382,965 B1 * | 5/2002 | Ruiz-Vela | A61C 7/02 433/4 |
| 6,474,988 B1 * | 11/2002 | Georgakis | A61C 7/04 433/4 |
| 2006/0064864 A1 * | 3/2006 | Meissner | A61C 7/02 29/426.5 |

(Continued)

*Primary Examiner* — Cris L Rodriguez
*Assistant Examiner* — Stephen Sparks (57) ABSTRACT

A tooth bracket extraction device which comprises a motor housed within a motor housing, and a motor shaft extending from the motor. A gear cover is fastened to the motor housing, and a first shaft is coupled to the motor shaft, where the first shaft receives the drive from the motor via the motor shaft. A first gear is attached to the first shaft, and a second shaft comprises a second gear, where the second shaft is in communication with the first shaft via engagement of the second gear to the first gear. A torque generated from the motor is transferred to the second shaft, and the second shaft comprises a head receiver member which is configured to receive and mount a plurality of heads. Each head is configured to transfer the torque to a bracket section attached to teeth, thereby removing the bracket section from the teeth.

17 Claims, 7 Drawing Sheets

(56) References Cited

U.S. PATENT DOCUMENTS

| | | | |
|---|---|---|---|
| 2007/0122763 A1* | 5/2007 | Farzin-Nia | A61C 7/02 433/4 |
| 2010/0269646 A1* | 10/2010 | Le Du | B25B 13/481 81/478 |
| 2010/0304330 A1* | 12/2010 | Rasmussen | B25B 13/462 433/147 |
| 2012/0077147 A1* | 3/2012 | Kalange | A61C 8/0089 433/114 |
| 2015/0079540 A1* | 3/2015 | Rek | A61C 1/148 433/122 |

* cited by examiner

TOOTH BRACKET EXTRACTION DEVICE AND METHODS FOR EXTRACTING A BRACKET SECTION FROM TEETH

BACKGROUND OF THE INVENTION

Debonding, by definition, is the procedure by which brackets and adhesive substance are removed from the surface of the tooth, and the tooth is restored to its previous condition. The objective of debonding is to achieve a tooth-surface similar to that prior to treatment without inflicting any type of iatrogenic damage. In order to perform this task, the adhesive substance over the teeth must be removed, and the brackets have to be freed.

Since next to dislodging the superficial enamel, debonding can also result in a great deal of wasted energy, we must consider a rather significant and major infrastructural method to prevent the aforesaid incidents from occurring due to the lack of using a correct method. Several methods have been offered for achieving a suitable debonding, whereby the performer must remove the remaining adhesive residue once the bracket has been removed.

For metal brackets numerous methods have been defined for bracket removal in utilizing various orthodontic pliers e.g. placing weingart or twin-beaked pliers over mesial and distal base of bracket, and separating it with a squeeze. This method is considered to be a soft method; however, it can readily bend the bracket in a way that it is rendered completely useless.

The other method includes placing the plier head over the bracket wings, and peeling the bracket off, but again in this method bracket can be easily deformed and unrecyclable. Moreover, Orthopli bracket removing 950 pliers may also be used in cases when the brackets are still ligated in their place. The brackets are pulled out one by one at an angle of 45° (degrees). This is a pretty fast method for removing; however, one disadvantage is that since brackets are fitted right under the gingival tie-wing, they use the gum to lean against and as result exert the debonding force onto the gum.

Diamond burs which are sometimes used in debonding are one of the weakest\methods because they are placed directly on the enamel where they apply their motion causing enamel abrasion. It should be noted that using uncontrolled manual methods can lead damage to the teeth, particularly the enamels. There is a need in the art presently for novel orthodontic bracket debonders and methods extracting a bracket section from teeth.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

A tooth bracket extraction device comprises a motor, a gear cover, a first shaft, a first gear a second shaft, and a second gear. The motor is housed within a motor housing, and a motor shaft extends from the motor. The gear cover is axially fastened to the motor housing, and the first shaft is coupled to the motor shaft and housed within the gear cover, where the first shaft receives the drive from the motor via the motor shaft. The first gear is distally attached to the first shaft, and the second shaft comprises a second gear, where the second shaft is in communication with the first shaft via engagement of the second gear to the first gear of the first shaft. A torque generated from the motor is transferred to the second shaft, and the second shaft comprises a head receiver member which is configured to receive and mount a plurality of heads. Each head is configured to transfer the torque to a bracket section attached to teeth, thereby removing the bracket section from the teeth.

In an embodiment, the bracket section is removed from the teeth by applying a force on the bracket section without touching the teeth. In an embodiment, the bracket section is removed from the teeth by applying a uniform force on four sides of the bracket section. In an embodiment, the application of uniform force on four sides of the bracket section prevents the force from being overtly exerted on a single point of the bracket section along the teeth, thereby preventing a gradual chipping and separation of the bracket section from the teeth. In an embodiment, the application of uniform force on four sides of the bracket section facilitates removal of the bracket section without any damage to one of the edges and stand of the bracket section.

In an embodiment, the tooth bracket extraction device operates on short cyclical torque actions, wherein the tooth bracket extraction device first loosens the stand of the bracket section, and then gradually increase the torque until the bracket section is detached from the teeth. In an embodiment, the tooth bracket extraction device further comprises a first manual mode of operation of the motor comprising steps of: setting a motor power, setting the duration of on-time in one direction of rotation of the motor, and setting an off-time prior to rotating the motor in the opposite direction.

In an embodiment, the tooth bracket extraction device further comprises a second manual mode of operation of the motor comprising steps of: setting a power in a primary step, setting a power in the final step, setting a duration of on-time of the motor in one direction of rotation, setting off-time prior to moving in the opposite direction of rotation, setting number of repeat steps, setting a power increase from one repeat step to the next step. In an embodiment, the motor starts to run based on a start power, and remains active for the duration of on-time. In an embodiment, during a period of the off-time of the motor, and prior to the rotation of the motor in the opposite direction, the motor stops, and then starts to run in the reverse direction under the same rate of power.

In an embodiment, the number of repeats is defined in a part for repeat step until the total completion of the repeat step. In an embodiment, the power of the repeat step is increased from one repeat step to another repeat step to the rate of the power step, and the second manual mode of operation of the motor is executed with a new power. In an embodiment, the tooth bracket extraction device provides application of cyclic rotational force along a longitudinal axis of the teeth, and none of tensile and peeling forces in between a base of the bracket section and an enamel of the teeth.

One aspect of the present disclosure is directed to a tooth bracket extraction device, comprising: a motor housed within a motor housing, and a motor shaft extending from the motor; a gear cover axially fastened to the motor housing; a first shaft coupled to the motor shaft and housed within the gear cover, the first shaft configured to receive the drive from the motor via the motor shaft; a first gear distally attached to the first shaft; and a second shaft comprising a second gear, the second shaft in communication with the first shaft via engagement of the second gear to the first gear of the first shaft, wherein a torque generated from the motor is transferred to the second shaft, and the second shaft comprises a head receiver member which is configured to receive and mount a plurality of heads, wherein each head is configured to transfer the torque to a bracket section attached to teeth, thereby removing the bracket section from the teeth.

In one embodiment, the bracket section is removed from the teeth by applying a force on the bracket section without touching the teeth. In another embodiment, the bracket section is removed from the teeth by applying a uniform force on four sides of the bracket section. In one embodiment, the application of uniform force on four sides of the bracket section prevents the force from being overtly exerted on a single point of the bracket section along the teeth, thereby preventing a gradual chipping and separation of the bracket section from the teeth. In one embodiment, the application of uniform force on four sides of the bracket section facilitates removal of the bracket section without any damage to one of the edges and stand of the bracket section. In another embodiment, the tooth bracket extraction device operates on short cyclical torque actions, wherein the tooth bracket extraction device first loosens the stand of the bracket section, and then gradually increase the torque until the bracket section is detached from the teeth.

In one embodiment, the tooth bracket extraction device further comprises a first manual mode of operation of the motor comprising: setting a motor power; setting the duration of on-time in one direction of rotation of the motor; and setting an off-time prior to rotating the motor in the opposite direction. In another embodiment, the tooth bracket extraction device further comprises a second manual mode of operation of the motor comprising: setting a power in a primary step; setting a power in the final step; setting a duration of on-time of the motor in one direction of rotation; setting off-time prior to moving in the opposite direction of rotation; setting number of repeat steps; and setting a power increase from one repeat step to the next step.

In one embodiment, the motor starts to run based on a start power, and remains active for the duration of on-time. In another embodiment, during a period of the off-time of the motor, and prior to the rotation of the motor in the opposite direction, the motor stops, and then starts to run in the reverse direction under the same rate of power. In one embodiment, the number of repeats is defined in a part for repeat step until the total completion of the repeat step. In one embodiment, the power of the repeat step is increased from one repeat step to another repeat step to the rate of the power step, and the second manual mode of operation of the motor is executed with a new power. In another embodiment, the tooth bracket extraction device provides application of cyclic rotational force along a longitudinal axis of the teeth, and none of tensile and peeling forces in between a base of the bracket section and an enamel of the teeth.

In one embodiment, the tooth bracket extraction device further comprises a first manual mode of operation of the motor comprising: setting a motor power; setting the duration of on-time in one direction of rotation of the motor; and setting an off-time prior to rotating the motor in the opposite direction; and a second manual mode of operation of the motor comprising: setting a power in a primary step; setting a power in the final step; setting a duration of on-time of the motor in one direction of rotation; setting off-time prior to moving in the opposite direction of rotation; setting number of repeat steps; and setting a power increase from one repeat step to the next step.

Another aspect of the present disclosure is directed to a method of extracting a bracket section from teeth. The method comprises: (a) providing tooth bracket extraction device, comprising; a motor housed within a motor housing, and a motor shaft extending from the motor; a gear cover axially fastened to the motor housing; a first shaft coupled to the motor shaft and housed within the gear cover, the first shaft configured to receive the drive from the motor via the motor shaft; a first gear distally attached to the first shaft; a second shaft comprising a second gear, the second shaft in communication with the first shaft via engagement of the second gear to the first gear of the first shaft; (b) generating a torque from the motor; (c) transferring the generated torque to the second shaft, and the second shaft comprises a head receiver member which is configured to receiving and mounting a plurality of heads on the second shaft via a head receiver member distally positioned on the second shaft; and (d) transferring the torque to a bracket section attached to teeth via each head to remove the bracket section from the teeth.

In one embodiment, the bracket section is removed from the teeth by applying a force on the bracket section without touching the teeth. In another embodiment, the bracket section is removed from the teeth by applying a uniform force on four sides of the bracket section. In one embodiment, the application of uniform force on four sides of the bracket section prevents the force from being overtly exerted on a single point of the bracket section along the teeth, thereby preventing a gradual chipping and separation of the bracket section from the teeth. In one embodiment, the application of uniform force on four sides of the bracket section facilitates removal of the bracket section without any damage to one of the edges and stand of the bracket section. In another embodiment, the tooth bracket extraction device operates on short cyclical torque actions, wherein the tooth bracket extraction device first loosens the stand of the bracket section, and then gradually increase the torque until the bracket section is detached from the teeth.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

DETAILED DESCRIPTION

The present invention generally relates to devices used in removal of brackets in dentistry, and more particularly relates to an electromechanical orthodontic bracket debonder which is configured to remove brackets from a teeth without damaging the teeth surface.

Diamond burs which are sometimes used in debonding are one of the weakest and methods because they are placed directly on the enamel where they apply their motion causing enamel abrasion. It should be noted that using uncontrolled manual methods can lead damage to the teeth, particularly the enamels. A great deal of effort has gone into promoting this device to the most ideal suitable level leading to an overall improvement in literally every feature. Furthermore, non-reliance of the device on none of the oral biological environment such as gingival and dental and their supporting tissues, vestibule and buccal mucosa next to application of suitable level of force with ail brackets in the form of repeat coupling with a determined domain, and through application of repeat movements and vibration causing a consequential fatigue in the adhesive, brackets are detached intact with less force and can be conveniently reused. The general result of all of this is the overall improvement in the condition of oral tissue and patient's convenience without applying peeling force.

Figure 1:
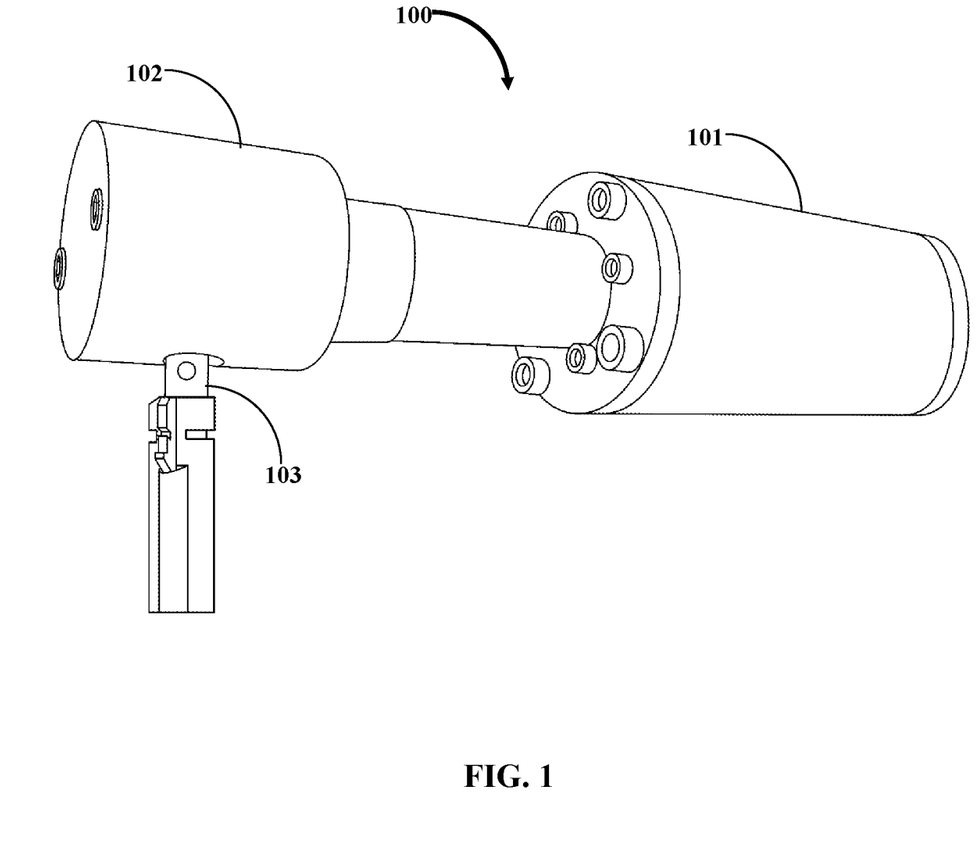
FIG. 1 exemplarily illustrates a top perspective view of the tooth bracket extraction device.
Figure 2:
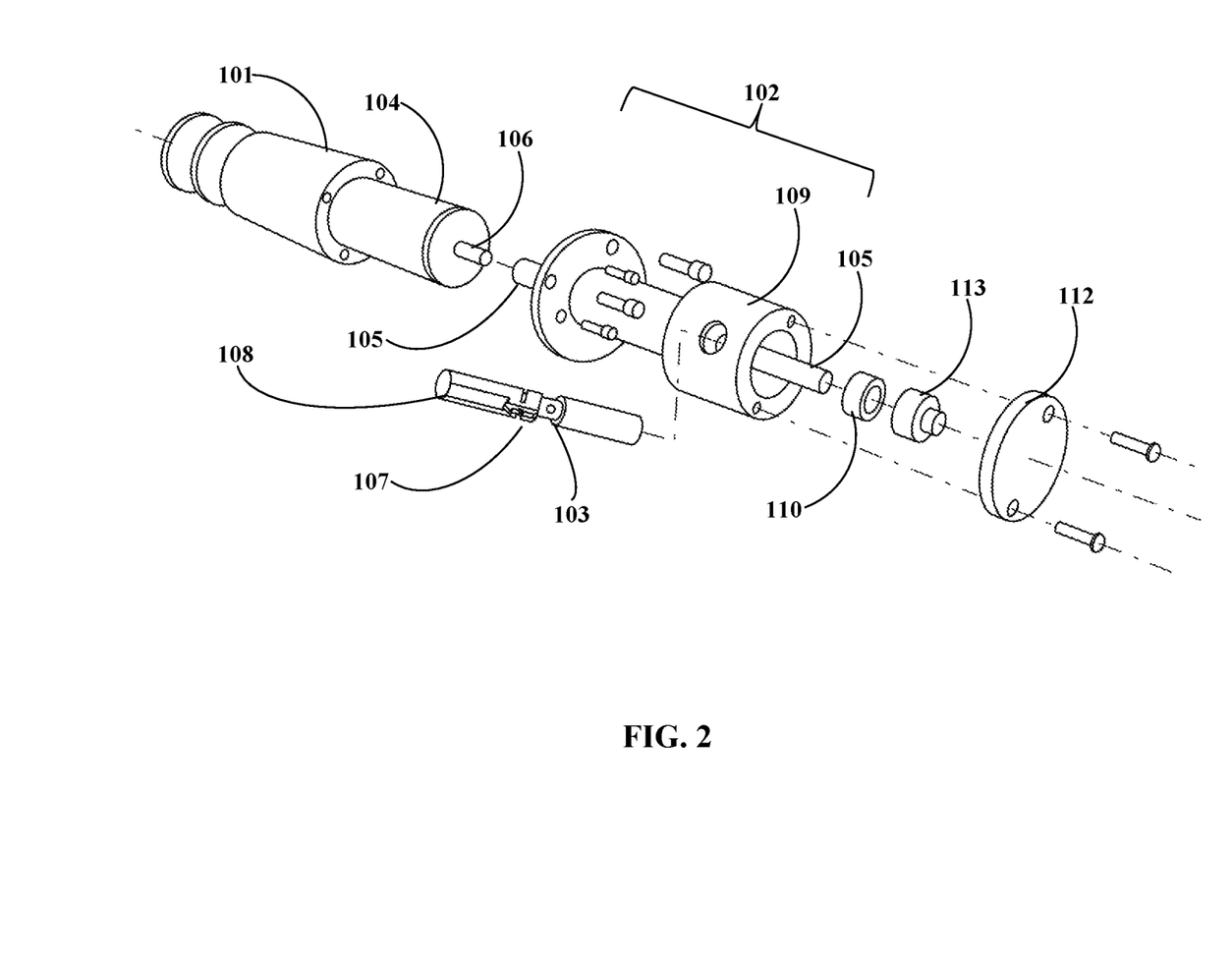
FIG. 2 exemplarily illustrates an exploded view of the tooth bracket extraction device.
Figure 3:
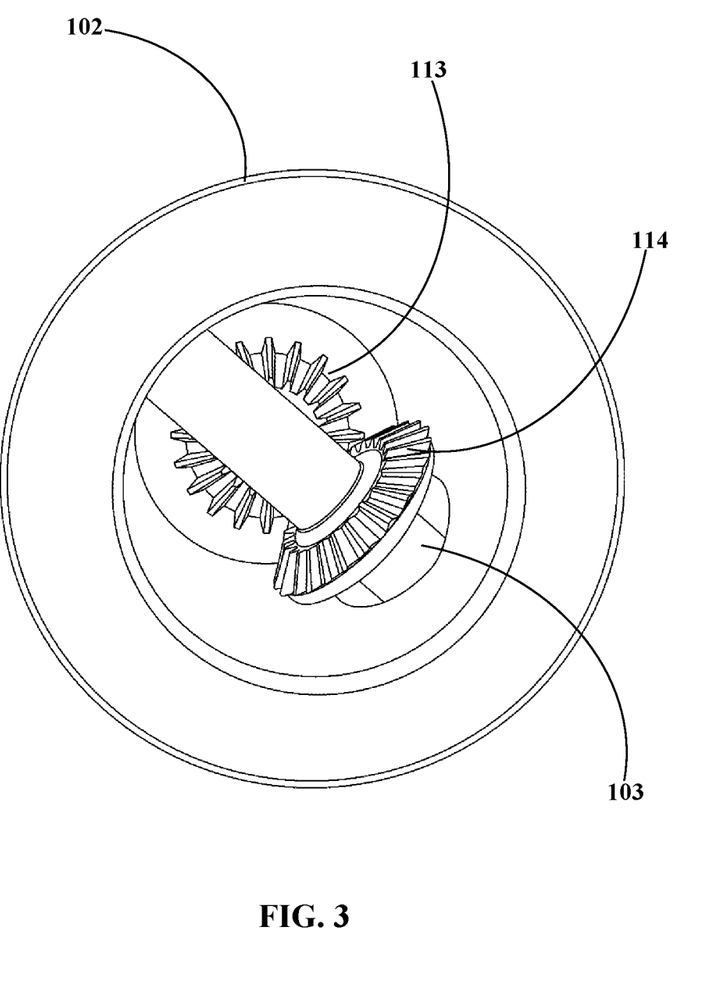
FIG. 3 exemplarily illustrates a customized gear mechanism for changing the direction of the output shaft.

FIG. 1 exemplarily illustrates a top perspective view of the tooth bracket extraction device 100. Referring to FIGS. 1 and 2, the tooth bracket extraction device 100 comprises a motor 104 housed within a motor housing 101, a gear cover 102, a first shaft 105, a first gear 113, a second shaft 103, and a second gear 114 as shown in FIG. 3. The motor 104 is housed within the motor housing 101, and a motor shaft 106 extends from the motor 104. The gear cover 102 is axially fastened to the motor housing 101, and the first shaft 105 is coupled to the motor shaft 106 and housed within the gear cover 102, where the first shaft 105 receives the drive from the motor 104 via the motor shaft 106.

The first gear 113 is distally attached to the first shaft 105, and the second shaft 103 comprises a second gear 114 as shown in FIG. 3, where the second shaft 103 is in communication with the first shaft 105 via engagement of the second gear 114 to the first gear 113 of the first shaft 105. A torque generated from the motor 104 is transferred to the second shaft 103, and the second shaft 103 comprises a head receiver member 107 which is configured to receive and mount a plurality of heads 108. Each head 108 is configured to transfer the torque to a bracket section attached to teeth, thereby removing the bracket section from the teeth.

In regard to the tooth bracket extraction device 100, through more attention and care for patient safety with respect to a healthier tooth tissue and reduction of enamel damage, the tooth bracket extraction device 100 has most certainly taken a major step forward. Some of the features which make this tooth bracket extraction device 100 ideal for clinical application include reduction of applied forces during debonding, control of movements and forces, patient comfort, pain reduction particularly in teeth with low bone support or with root resorption, capable of conducting various rotational patterns (high and low torques as well as vibration) next to many other advantages such as complete preservation of brackets after applied function. All of the aforementioned features are showing indication of attention to the presentation of the tooth bracket extraction device 100 in a clinical environment.

Moreover, clinical and para-clinical studies, and the resulting accumulated experiences confirm the items of discussion being addressed, and therefore no serious complications have been observed. The surfaces of the components of the tooth bracket extraction device 100 are sterilized at every level of function, particularly their removable heads 108, and sterilization procedures do no effect their quality. High capability of heads 108 to fit perfectly into the bracket slots whether the slot is vertical or horizontal is another sign of the importance of the tooth bracket extraction device 100.

It should also be stated that the applicability of numerous different heads 108 which are firmly fixed into place by existing magnets in the cover of terminal or second shaft 103 significantly increase the performance and effectiveness of the tooth bracket extraction device 100 when coupled with diverse systems such as ceramic and metal. Detaching the bracket is done by applying rotational and coupling forces. In fact, this force replaces the compressive force as well.

The manner of applying the force in these methods using the tooth bracket extraction device 100 has several advantages. In an embodiment, in a first method, the force is only applied onto the bracket section, and the tools applying the force do not touch the teeth. In an embodiment, in a second method, the force is applied uniformly to four sides of the bracket section which not only does it facilitate the detachment of the bracket, but it also prevents the force from being overtly exerted on a single point, thereby preventing its gradual chipping and separation. Third advantage is the fact that by coupling the tooth bracket extraction device 100 firmly to the bracket section and applying equal force to its four corners, therefore the tooth bracket extraction device 100 is able to remove the bracket section without any damage to its edges or stand.

In an embodiment, the torque function of the tooth bracket extraction device 100 is completely smart, and operates on the principle of fatigue, whereby the short cyclical torque actions, first loosen a stand of the bracket section, and then slowly increase the torque until the bracket section is detached from the teeth. After work is finished, the system instantly shuts off the motor 104 so that unwanted movements which may harm the patient do not occur.

This method of applying the torque has many advantages, among them debonding from teeth with the minimum possible force in a way that the patient does not even feel the detachment, insubstantial damage to the root because the forces are applied in the shortest amount of time possible. As a matter of fact, there is no noticeable change in the formation of tissues encircling the root, and they will not get damaged. Since forces stop immediately after detachment of the bracket section, there will not be any forced impacts or lunging of the bracket section. The force is applied in complete proportion to each tooth and the strength of its bracket section which is debonded in the best way possible.

Another feature which needs mentioning is the full aluminum cover of the tooth bracket extraction device 100 which not only was more suitable for the prototype, but it may also be disinfected as required. However, even with all these features the design of the tooth bracket extraction device 100 is quite compact, and therefore can be held easily in the dentist's hands, and also take less space to make working more convenient. Furthermore, a disposable head 108 enables the dentist to use different heads 108 for various bracket sections, and to disinfect and replace those heads 108 as required. Finally, high dependability, and more torque than required have all been taken into account in selecting the motor 104 for the tooth bracket extraction device 100.

FIG. 2 exemplarily illustrates an exploded view of the tooth bracket extraction device 100. To assemble the tooth bracket extraction device 100, first a set of bearings inside the shell or the gear cover 102 are fitted into the outer race by applying a few gentle strokes. Next, the first shaft 105 that extends from the motor shaft 106, with a pin-mounted gear 113 already installed is fitted into the bearing 110 from above which until the step sits on the first shaft 105 is placed is inserted into the outer race.

Figure 4A:
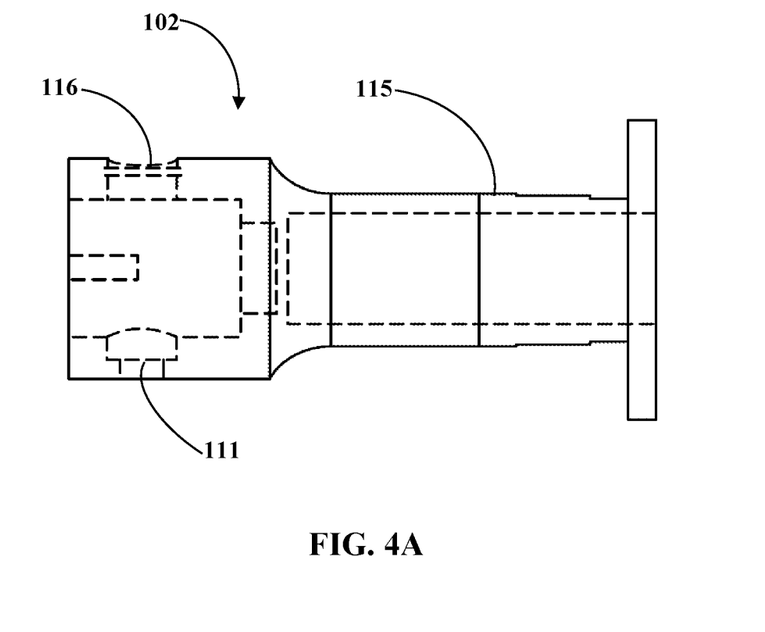
FIG. 4A exemplarily illustrates a side view of the gear and bushing cover.

In the next stage, the second shaft 103 which is the main output shaft of the tooth bracket extraction device 100 is inserted into the shell 109 of the gear cover 102 from the side. As the second shaft 103 is inserted inside the second gear 114 as shown in FIG. 3, which is housed within the wall is placed on top. Once the pin for the second gear 114 has been inserted, the second bearing 111 of second shaft 103 is placed on top. An internal retaining ring is used in front of third bearing 116 as shown in FIG. 4A, to keep it from falling out.

After everything has been attached, and the gear has been properly lubricated, the cap 112 is put in place for total protection. When all the steps mentioned above are completed, the motor 104 with the bushing already mounted is tightened to gear cover 102 using four screws. Also, the set screws for connecting the bushing to the first shaft 105 are tightened using an Allan-wrench through the hole considered. Finally, the motor housing 101 is put on the motor 104, and tightened to gear cover 102 using four screws so that the tooth bracket extraction device 100 is completely assembled.

In one aspect, the present disclosure is directed to a tooth bracket extraction device. The device comprises a motor housed within a motor housing, and a motor shaft extending from the motor; a gear cover axially fastened to the motor housing; a first shaft coupled to the motor shaft and housed within the gear cover, the first shaft configured to receive the drive from the motor via the motor shaft; a first gear distally attached to the first shaft; and a second shaft comprising a second gear, the second shaft in communication with the first shaft via engagement of the second gear to the first gear of the first shaft, wherein a torque generated from the motor is transferred to the second shaft, and the second shaft comprises a head receiver member which is configured to receive and mount a plurality of heads, wherein each head is configured to transfer the torque to a bracket section attached to teeth, thereby removing the bracket section from the teeth.

Electrical Dimension hardware specifications of the tooth bracket extraction device 100 include: an Electrical board, a Double-sided PCB, an AVR ATMega 16 controller, a 12V DC/2 amp, an LCD for monitoring device status, a driver with DC motor of Type: L298, Output: 12V (max. 2 amp), a Linking to computer via RS232 (including a USB-Serial convertor), a direct programming capability via USBASP, a control pedal and performance selection switch software and capabilities, independent performance using the pedal, a performance selection switch and LCD (including the capability of multi-programming), a remote control via computer and user interface by connecting a USB, a connection status monitoring, a selection among triple default modes.

There are two modes of operation, namely a first manual mode and a second manual mode. In the first manual mode, the possibility of defining a sweep ring by setting the following parameters that are repeated with each pedal use. The steps involve: setting a power for the motor 104, setting the duration of on-time in one direction of rotation, and setting an off-time prior to moving in the opposite direction of rotation. In the second manual mode, an ability of defining a series of repeat steps with the possibility of setting the parameters below which are repeated with each pedal use: such as, the setting a power in the primary step, setting a power in the final step, setting a duration of on-time in one direction of rotation, setting off-time prior to moving in the opposite direction of rotation, setting number of repeat steps, setting a power increase from one repeat step to the next.

As for the considerations, in an embodiment, in the aforementioned method, the motor 104 starts to run based on the start power, and remain active for the duration of on-time. For a period of off-time, and prior to moving in the opposite direction, the motor 104 stops, and then starts to run in the reverse direction under the same rate of power. The number of repeats for this function is defined in the part for repeat step until the total completion of the repeat step. Next, the power of this step is increased from one repeat step to another to the rate of the power step, and the above-stated process of second manual mode of operation of the motor 104 is executed with a new power.

In an embodiment, the tooth bracket extraction device 100 provides application of cyclic rotational force instead of shearing force along the longitudinal axis of the teeth or tensile or peeling forces in between bracket base and enamel. Advantage: Application of tension equal to 0.57 to 4.07 MPa instead of debonding force (6.18 to 6.68). The tooth bracket extraction device 100 provides application of gentle force to the root and the alveolar cavity resulting in less pain for the patient. The tooth bracket extraction device 100 provides creation of adhesive fatigue instead of sudden shearing of filaments existing in the adhesive when debonding the bracket.

The tooth bracket extraction device 100 provides bracket debonding without deformation, and ability to use after sterilization with respect to certain bracket sections and cost-effectiveness. The tooth bracket extraction device 100 prevents damage or enamel crack in comparison to other conventional methods which are almost always followed by enamel cracks. The tooth bracket extraction device 100 facilitates bracket debonding in posterior teeth in comparison to the conventional methods. The tooth bracket extraction device 100 facilitates convenience of use for the dentist, and reduces patient discomfort in case of user negligence in comparison to other conventional methods.

FIG. 3 exemplarily illustrates a customized gear mechanism for changing the direction of the output shaft or the second shaft 103. In addition to the above-described features, many other factors have been considered in designing the tooth bracket extraction device 100. One of these important factors is the capability to change the direction of the torque. This has been achieved by placing a 90 degrees gear, or the second gear 114 in communication with the first gear 113 towards the end part of the tooth bracket extraction device 100 where it is encased by the gear cover 102 so the dentist can conveniently and with more control complete the detachment process. One advantage that this change offers is the ideal angle of the placement of the tooth bracket extraction device 100 around the mouth which makes working rather easy.

Referring to FIG. 2 and FIGS. 4A-9, out of eighteen pieces, ten are pre-fabricated and eight are manufactured. Most of the components are made of, for example, aluminum 7000, cut with lathe and milling machine. The main part of the tooth bracket extraction device 100 is the gear cover 102 which encases the bushing and the first gear 113 and the second gear 114 as well as all the ball bearings 110 and 111, as shown in FIGS. 2 and 4A. As mentioned this part is completely made of aluminum cut into shape using lathe and milling machine.

Also, an aluminum cap 112 has to protect the gears 113 and 114 and to keep the tooth bracket extraction device 100 in sanitary condition has been placed at the end of the gear cover 102. The next part is the motor housing 101 which houses the motor 104, and also curbs and controls its rotation. This aluminum piece is attached on one side to the gear cover 102, and its other end is attached to the insulated wiring box. Power transmission from the motor shaft 106 to the final heads 108 is done through a series of bushings and gears 113 and 114 as further described in detail.

Figure 4B:
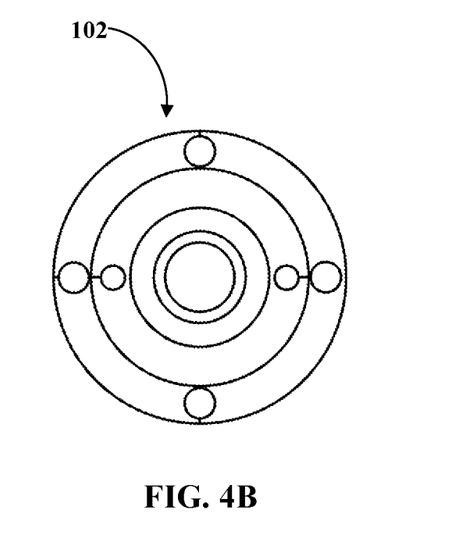
FIG. 4B exemplarily illustrates a front perspective view of the gear and bushing cover.

FIG. 4A exemplarily illustrates a side view of the gear cover 102, and FIG. 4B exemplarily illustrates a front perspective view of the gear cover 102. This part is the main and the most important part of the tooth bracket extraction device 100 which is screwed to the motor housing 101 on four sides where four holes have also been drilled in an angle difference of 45 degrees to hold the motor 104 in place. Moreover, there is a longitudinal hole in a diameter of 20 millimeter (mm) and length of 50 mm inside the gear cover 102 that is used to house the power transmission bushing. Right on top of this hole where the set screws are fastened there is a hole for the passage of the Allen screw which is used to tighten the bushing to the second shaft 103.

After the longitudinal hole, a bearing housing 115 in the diameter of 13 mm has been considered to set in the first bearing holder behind which there is a 2 mm step for holding the bearing. Directly in front of this part, a hole in the diameter of 20 mm and length of 25 mm has been drilled. Also, by creating a 10 mm vertical hole in this section, using a four-jaw chuck, makes it possible for the aluminum shell on either side to house the two ball bearings inside itself leading to the curbing of the action of the second shaft 103 from two sides. Some aluminum shell has been left intact behind one of the bearings 111 to somehow try and curb its action from behind. A retaining ring casing has been embedded on the outer part of the other bearing 116 as shown in FIG. 4A, to prevent it from moving outwards. Finally, to curb and control these three ball bearings 110, 111, and 116, some steps have also been embedded on the shafts 105 and 103 to contain them.

Figure 5:
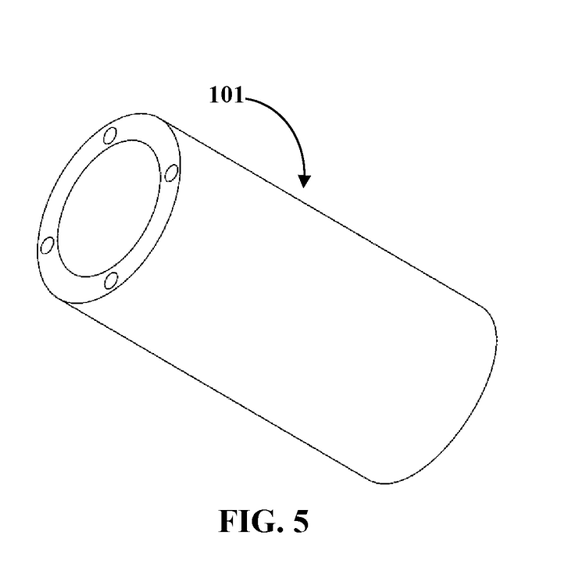
FIG. 5 exemplarily illustrates a front perspective view of the motor cover.

FIG. 5 exemplarily illustrates a front perspective view of the motor housing 101. This piece which is also completely made of aluminum protects the motor 104 against the work elements, and maintains the electronic section of the engine end. Furthermore, due to its thickness of 43 mm, this part can also be used as a handle. A hole in the length of 31 mm has been drilled all the way through this piece which has been bored an additional 0.3 mm to allow for a better fitting to the motor 104. The piece is attached to the gear cover 102 on one end using four screws, and is attached to terminal insulation whose job is to protect the electrical section of the tooth bracket extraction device 100.

Figure 6:
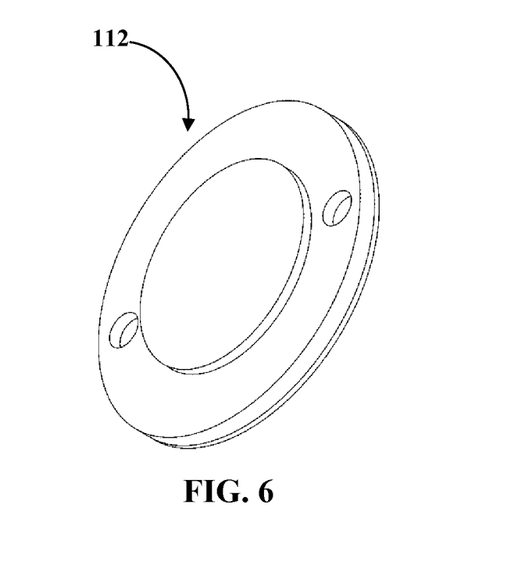
FIG. 6 exemplarily illustrates a front perspective view of the gear cap.

FIG. 6 exemplarily illustrates a front perspective view of the gear cap 112. The gear cap 112 is also made of aluminum, and its main function is to prevent dust and other particles from getting into the tooth bracket extraction device 100. A protruded edge has been considered at the end so that the piece is held firmly in place. To attach the gear cap 112 to gear cover 102, two flathead screws are used.

Figure 7:
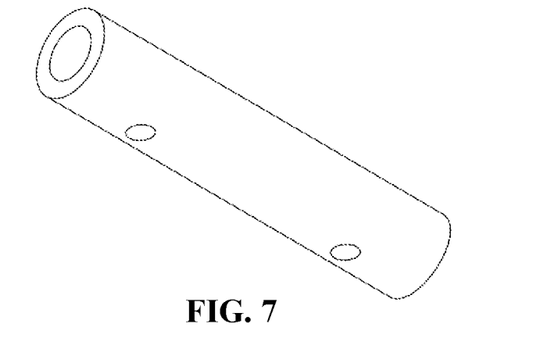
FIG. 7 exemplarily illustrates a front perspective view of the bushing.

FIG. 7 exemplarily illustrates a front perspective view of the bushing. The bushing is made of aluminum has a 6 mm hole drilled all the way through. The bushing house the motor shaft 106 on one end and houses the gear shaft or the first shaft 105 at the other. Two set screws have been embedded in the vertical direction of the bushing and are tightened to the smooth parts of the motor shaft 106 and gear shaft 105 to allow for the proper torque transmission.

Figure 8:
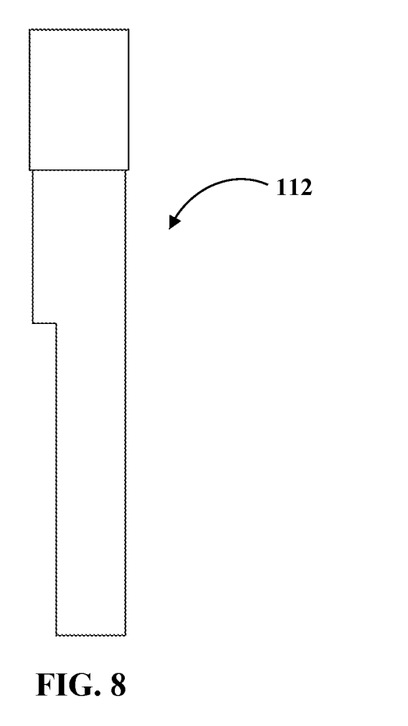
FIG. 8 exemplarily illustrates a side perspective view of the first shaft.

FIG. 8 exemplarily illustrates a side perspective view of the first shaft 105. The first shaft 105 is made of stainless steel and is actually a 1.4 inch shaft which allows a better coupling with inch gears. The first part of the first shaft 105 is placed inside the bushing, and its specifically smoothed spot is used to tighten in the set screws. The part of the bushing which is left out is first placed inside a bearing in order to have it curbed in an appropriate manner. Finally, at the end part right after the shaft step, there is bevel inch gear which has a conical pin mounted on top.

Figure 9:
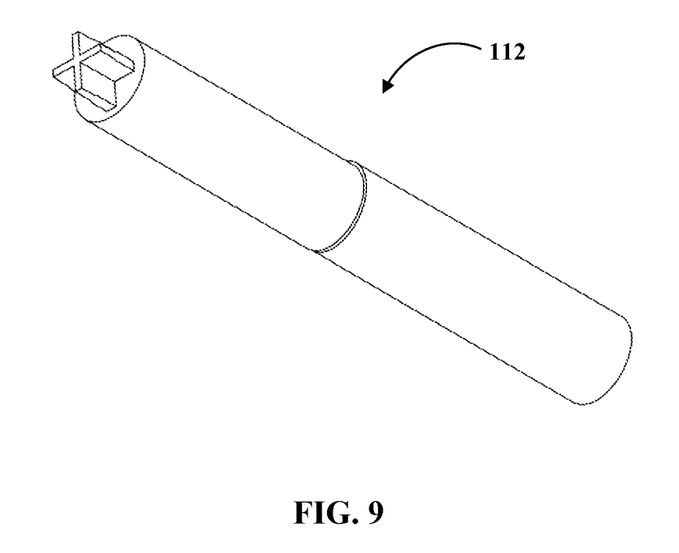
FIG. 9 exemplarily illustrates a side perspective view of the second shaft.

FIG. 9 exemplarily illustrates a side perspective view of the second shaft 103. The second shaft 103 is very accurate and milled to be fit in bracket slots. The second shaft 103 fixes through the tooth bracket extraction device 100 by a magnet force so changing the heads 108 is provided by this method. The tooth bracket extraction device 100 provides application of sequential vibrational and rotational forces when debonding, and a proper fitting into bracket slots in order to apply force. The tooth bracket extraction device 100 facilitates electronic function of debonding without any manual interference, and application of cyclic coupling force in specific and diverse domains when debonding.

The tooth bracket extraction device 100 provides changeable device heads 108 for different bracket variations. The tooth bracket extraction device 100 provide: (1) application of proper force to the tooth in terms of the status of the alveolar socket, (2) bonding technique and bonding materials, (3) base of the brackets, (4) enamel structure, and (4) the ability to select the required debonding force in terms of type of tooth, both anterior or posterior. The tooth bracket extraction device 100 provides total patient comfort during debonding, no risk of damage to the oral and tooth tissue due to the absence of user error which may occur in other conventional methods, and convenience and assurance of application of the method for special cases and syndromic patients as compared to other conventional methods.

The present disclosure is, in one example, directed to a method of extracting a bracket section from teeth. The method comprises: (a) providing tooth bracket extraction device, comprising; a motor housed within a motor housing, and a motor shaft extending from the motor; a gear cover axially fastened to the motor housing; a first shaft coupled to the motor shaft and housed within the gear cover, the first shaft configured to receive the drive from the motor via the motor shaft; a first gear distally attached to the first shaft; a second shaft comprising a second gear, the second shaft in communication with the first shaft via engagement of the second gear to the first gear of the first shaft; (b) generating a torque from the motor; (c) transferring the generated torque to the second shaft, and the second shaft comprises a head receiver member which is configured to receiving and mounting a plurality of heads on the second shaft via a head receiver member distally positioned on the second shaft; and (d) transferring the torque to a bracket section attached to teeth via each head to remove the bracket section from the teeth.

The bracket section may be removed from the teeth by applying a force on the bracket section without touching the teeth. The bracket section may be removed from the teeth by applying a uniform force on four sides of the bracket section. The application of uniform force on four sides of the bracket section, in one example, can prevent the force from being overtly exerted on a single point of the bracket section along the teeth, thereby preventing a gradual chipping and separation of the bracket section from the teeth.

The foregoing examples have been provided merely for the purpose of explanation and are in no way to be construed as limiting of the present concept disclosed herein. While the concept has been described with reference to various embodiments, it is understood that the words, which have been used herein, are words of description and illustration, rather than words of limitation. Further, although the concept has been described herein with reference to particular means, materials, and embodiments, the concept is not intended to be limited to the particulars disclosed herein; rather, the concept extends to all functionally equivalent structures, methods and uses, such as are within the scope of the appended claims. Those skilled in the art, having the benefit of the teachings of this specification, may affect numerous modifications thereto and changes may be made without departing from the scope and spirit of the concept in its aspects.

The invention claimed is:

1. A tooth bracket extraction device, comprising:
a motor housed within a motor housing, and a motor shaft extending from the motor;
a gear cover axially fastened to the motor housing;
a first shaft coupled to the motor shaft and housed within the gear cover, the first shaft configured to receive a drive from the motor via the motor shaft;
a first gear distally attached to the first shaft; and
a second shaft comprising a second gear, the second shaft in communication with the first shaft via engagement of the second gear to the first gear of the first shaft, wherein a torque generated from the motor is transferred to the second shaft, and the second shaft comprises a head receiver member which is configured to receive and mount a plurality of heads, wherein each head is configured to transfer the torque generated from the motor to apply a uniform force on four sides of a bracket section attached to teeth, thereby removing the bracket section from the teeth.

2. The tooth bracket extraction device of claim 1, wherein the bracket section is removed from the teeth by applying the uniform force on the bracket section without touching the teeth.

3. The tooth bracket extraction device of claim 1, wherein the application of uniform force on four sides of the bracket section prevents the force from being overtly exerted on a single point of the bracket section along the teeth, thereby preventing a gradual chip-ping and separation of the bracket section from the teeth.

4. The tooth bracket extraction device of claim 1, wherein the application of uniform force on four sides of the bracket section facilitates removal of the bracket section with-out any damage to one of the edges and stand of the bracket section.

5. The tooth bracket extraction device of claim 1, operates on short cyclical torque actions, wherein the tooth bracket extraction device first loosens the stand of the bracket section, and then gradually increase the torque until the bracket section is detached from the teeth.

6. The tooth bracket extraction device of claim 1, further comprising a first manual mode of operation of the motor comprising:
setting a motor power;
setting a duration of on-time in one direction of rotation of the motor; and
setting an off-time prior to rotating the motor in the opposite direction.

7. The tooth bracket extraction device of claim 6, further comprising a second manual mode of operation of the motor comprising:
setting a power in a primary step;
setting a power in a final step;
setting a duration of on-time of the motor in one direction of rotation;
setting off-time prior to moving in the opposite direction of rotation;
setting number of repeat steps; and
setting a power increase from one repeat step to a next step.

8. The tooth bracket extraction device of claim 7, wherein the motor starts to run based on a start power, and remains active for the duration of on-time.

9. The tooth bracket extraction device of claim 7, wherein during a period of the off-time of the motor, and prior to the rotation of the motor in the opposite direction, the motor stops, and then starts to run in the reverse direction under the same rate of power.

10. The tooth bracket extraction device of claim 7, wherein the number of repeats is defined in a part for repeat step until total completion of the repeat step.

11. The tooth bracket extraction device of claim 8, wherein the power of the repeat step is increased from one repeat step to another repeat step to a rate of the power step, and the second manual mode of operation of the motor is executed with a new power.

12. The tooth bracket extraction device of claim 8, provides application of cyclic rotational force along a longitudinal axis of the teeth, and none of tensile and peeling forces in between a base of the bracket section and an enamel of the teeth.

13. A method of extracting a bracket section from teeth, the method comprising:
providing tooth bracket extraction device, comprising:
a motor housed within a motor housing, and a motor shaft extending from the motor;
a gear cover axially fastened to the motor housing;
a first shaft coupled to the motor shaft and housed within the gear cover, the first shaft configured to receive a drive from the motor via the motor shaft;
a first gear distally attached to the first shaft; and
a second shaft comprising a second gear, the second shaft in communication with the first shaft via engagement of the second gear to the first gear of the first shaft;
generating a torque from the motor;
transferring the generated torque from the motor to the second shaft, and the second shaft comprises a head receiver member which is configured to receiving and mounting a plurality of heads on the second shaft via a head receiver member distally positioned on the second shaft; and
transferring the torque to apply a uniform force on four sides of a bracket section attached to teeth via each head to remove the bracket section from the teeth.

14. The tooth bracket extraction device of claim 13, wherein the bracket section is removed from the teeth by applying the uniform force on the bracket section without touching the teeth.

15. The tooth bracket extraction device of claim 14, wherein the application of uniform force on four sides of the bracket section prevents the force from being overtly exerted on a single point of the bracket section along the teeth, thereby preventing a gradual chipping and separation of the bracket section from the teeth.

16. The tooth bracket extraction device of claim 14, wherein the application of uniform force on four sides of the bracket section facilitates removal of the bracket section with-out any damage to one of the edges and stand of the bracket section.

17. The tooth bracket extraction device of claim 14, operates on short cyclical torque actions, wherein the tooth bracket extraction device first loosens the stand of the bracket section, and then gradually increase the torque until the bracket section is detached from the teeth.

* * * * *